United States Patent [19]
Wang et al.

[11] Patent Number: 5,642,278
[45] Date of Patent: Jun. 24, 1997

[54] METHOD AND APPARATUS FOR TEMPERATURE AND PRESSURE COMPENSATION OF PNEUMATIC MANIFOLDS

[75] Inventors: Tak Kui Wang, Havertown, Pa.; Paul Bryce Welsh, Wilmington, Del.; Edwin E. Wikfors, Landenberg, Pa.

[73] Assignee: Hewlett-Packard Co., Palo Alto, Calif.

[21] Appl. No.: 367,986

[22] Filed: Jan. 3, 1995

[51] Int. Cl.[6] ................................................. G05B 17/02
[52] U.S. Cl. ..................... 364/149; 364/498; 364/510; 96/102
[58] Field of Search .................. 364/149–151, 364/509, 510, 496, 497, 498, 499, 500, 557, 558; 95/1, 14, 15, 25; 96/101, 102, 103; 55/210, 270, 271, 274; 73/861.52, 861.01

[56] References Cited

U.S. PATENT DOCUMENTS

| | | | |
|---|---|---|---|
| 4,164,206 | 8/1979 | Toelle | 364/431.06 X |
| 4,962,662 | 10/1990 | Berger | 73/23.42 |
| 4,994,096 | 2/1991 | Klein et al. | 95/15 |
| 5,108,466 | 4/1992 | Klein et al. | 95/1 |
| 5,146,941 | 9/1992 | Statler | 137/8 |
| 5,329,966 | 7/1994 | Fenimore et al. | 137/613 |
| 5,445,035 | 8/1995 | Delajoud | 73/861.52 |

OTHER PUBLICATIONS

Lucas Control System Products, NOVASENSOR Sales Brochure, includees: Short Form Catelog, NPI Series All Media Solid State Sensor Pressure Transducer — Medium Pressure and High Pressure Brochures, NPH Series Solid State Pressure Sensor — Medium Pressure, and Low Pressure Brochures, NAS Series solid State Accelerometer Signal Conditioned. Output Brochure, NAC Series Silicon Accelerometers–Ceramic Packages Brochure; dates unknown.

Primary Examiner—Joseph Ruggiero
Attorney, Agent, or Firm—Richard F. Schuette

[57] ABSTRACT

A simplified method and apparatus for electronic pressure control with compensation for current operating temperature and pressures in which computer memory is employed for storing a plurality of firmware models which characterize the effects of temperature and pressure variations on (1) fluid flow through the flow restrictor, (2) the temperature sensor, and (3) the pressure sensor, so that control signals can be generated which compensate a plurality of thermally coupled sensors for changes in current operating temperatures and pressures.

10 Claims, 9 Drawing Sheets

METHOD AND APPARATUS FOR TEMPERATURE AND PRESSURE COMPENSATION OF PNEUMATIC MANIFOLDS

FIELD OF THE INVENTION

The present invention relates to methods and apparatus for providing distribution and regulation of fluids and, more particularly, to a temperature compensated pneumatic manifold for accurate control of fluid pressure and flow.

BACKGROUND OF THE INVENTION

It is well known that fluid flow may be regulated electronically by employing an electronically controlled fluid regulator for adjusting the pressure of the fluid upstream of a flow restrictor in response to a control signal generated by a pressure sensor positioned upstream of the flow restrictor. In the automotive field, such fluid regulation might be employed in the intake manifold or fluid distribution system of a gasoline engine. In the field of gas chromatography, the gas chromatograph (GC) detectors require accurately regulated fluid supplies, the distribution of which is performed by a pneumatic manifold.

Figure 1:
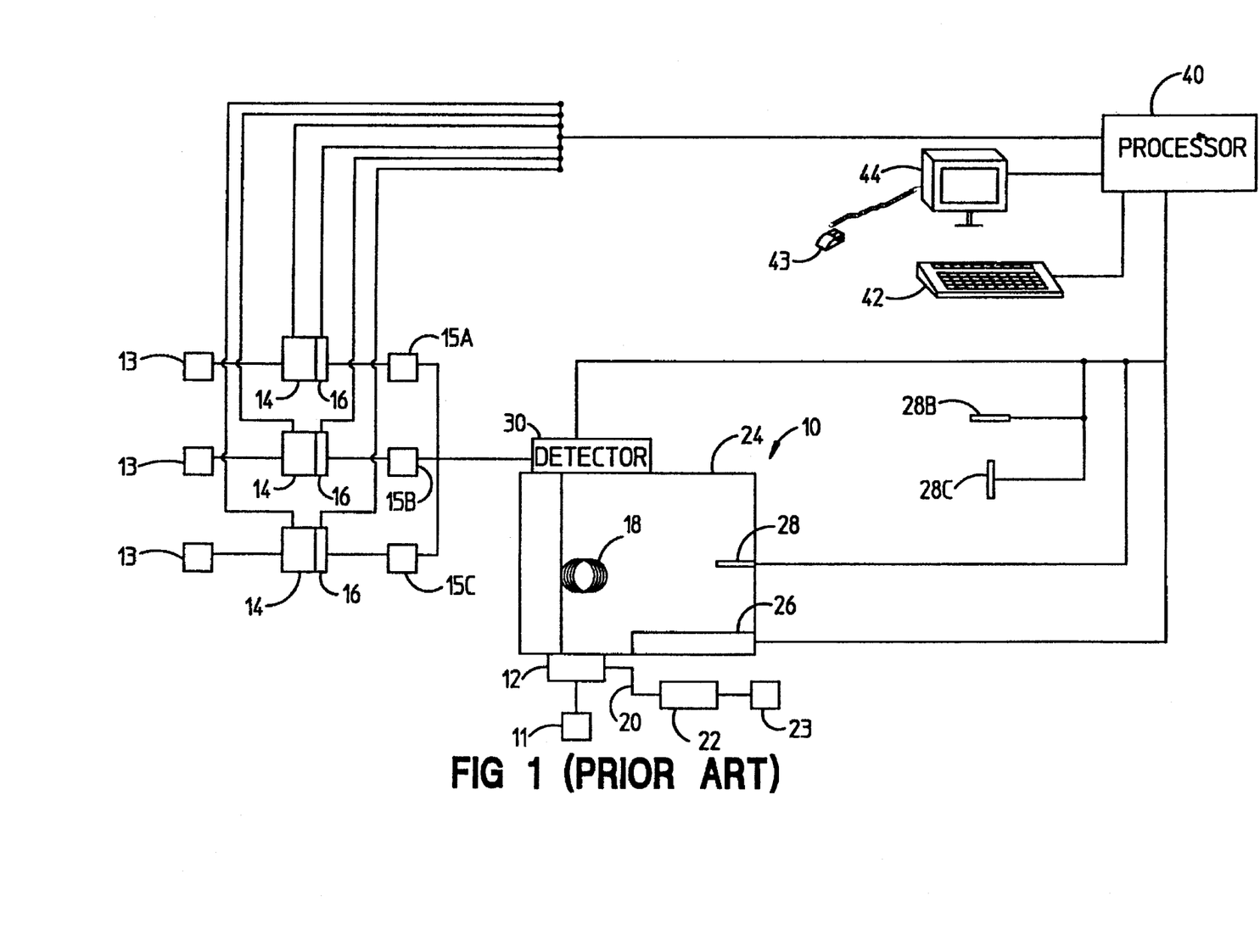
FIG. 1 is a simplified schematic representation of a prior art gas chromatograph having three detectors with electronically controlled support fluids.

A gas chromatographic apparatus, well known in the prior art, is shown in FIG. 1. The chromatograph 10 is arranged in a forward pressure regulated design suitable for direct injection. The detector 30 can be any of the GC detectors known in the art Typically, the detector 30 determines the magnitude of the physicochemical property over time. The performance of many chromatographic detectors is dependent upon the flow rate or pressure of the support fluid employed. By modifying the pressure or flow rate of the detector support fluids, one can for example, optimize detector sensitivity in a flame photometric detector (FPD) or flame ionization detector (FID), or to minimize solvent quenching of an nitrogen phosphorous detector (NPD) bead.

As well known in the prior art, and as illustrated in FIG. 1, a typical detector pneumatic manifold supplies three fluid sources 13a, 13b, 13a to three separate valves 14a, 14b, 14c. The valves serve to control both the pressure and the flow rate of the support fluid components. Flow through flow restrictors 15a, 15b, 15c provide back pressure such that sensors 16a, 16b, 16c can generate stable electronic signals in relation to the pressures or the flow rates of the component fluids. Pressure signals are provided to a processor 40, which in turn provides control signals to the valves 14a, 14b, 14c to regulate the pressure of the component fluids.

The processor 40 can maintain the pressure at some desired level by generating control signals directing the operation of the valves 14a–c. Since the generated control signals are in a digital form, they are converted to analog form by a digital to analog converter and appropriately amplified by an amplifier prior to transmission to valves 14a–c. The fluid pressures as sensed by the sensors 16a–c are provided to the processor 40 by first converting the analog signals generated by the pressure sensors 16a–c from an analog to digital signal by an A/D converter. The digital signals generated by the converter are supplied to the processor 40.

Unfortunately, the flow rate of a fluid through the flow restrictors 15a–c is unstable and varies with flow restrictor construction, the type of fluid flowing through the flow restrictor, the temperature of the fluid (essentially the manifold temperature) and the pressure of the fluid both upstream and downstream from the flow restrictor. Additionally, the pressure sensors 16a–c are sensitive to variations in temperature which can lead to errors in flow regulation. There exists a need for more stable detector fluid flows and reduced manifold temperature variations to provide better chromatographic area repeatability.

One method for eliminating temperature sensitivity is to enclose the flow sensing and controlling devices in a controlled heated zone constructed with thermally insulating material. Temperature sensors and heaters inside the heated zone provide feedback to maintain the flow restrictor and pressure sensor temperatures constant and thereby remove temperature as an error-producing variable.

Unfortunately, the incorporation of a heated zone increases manufacturing costs related to instrument calibration and components. Additionally, instrument reliability is reduced as the components required to regulate a heated zone are more likely to fail with continual operation at manifold temperatures higher than ambient. Furthermore, a heated zone requires a long start-up time to stabilize prior to instrument operation.

Another technique for correcting the inaccuracy of the pressure flow relationship due to flow restrictor variation and temperature dependencies is to perform extensive, multi-point calibrations at a very large number of different operating temperatures and pressures. The results of such calibrations are saved in an EEPROM and employed for adjusting the feedback signal to the control valve. The calibration points relate pressure sensor signals outputs, ambient pressure signal outputs, and a temperature signal to fluid flow rate through the flow restrictor. A separate set of calibrations is required for each fluid and flow restrictor combination. Unfortunately, the cost of such calibrations make this technique commercially unreasonable.

A need exists for a pneumatic manifold design which automatically compensates fluid flows for ambient temperature and pressure changes without the use of a heated zone.

SUMMARY OF THE INVENTION

The present invention provides a simplified method and apparatus for electronic pressure control with ambient temperature and pressure compensation of detector fluid pressure and flow. A pneumatic manifold includes a plurality of thermally coupled sensors which measure and generate signals related to fluid pressure at both the high pressure side and low pressure side of a flow restrictor, as well as the temperature of the flow restrictor and the pressure sensors.

Computer memory is employed for storing a plurality of firmware models which characterize the effects of temperature and pressure variations on (1) fluid flow through the flow restrictor, (2) the temperature sensor, and (3) the pressure sensor. For example, fluid flow through the flow restrictor may be characterized as:

$$Q = [\alpha f] * \frac{(P_s + P_a)^2 - P_a^2}{T_f^{\,p}} + [\beta f] * \frac{P_s}{T_f^{\,5}}$$

In order to determine the unknown constants, the pneumatic manifold is operated in a pneumatic manifold carrier at a plurality of known temperatures and pressures such that a plurality of sensor output voltages can be measured. The constants $\alpha f$ and $\beta f$ from the flow equations are obtained by substituting the measured sensor output voltages into the Flow Restrictor Equation and solving for the constants.

Current operating temperatures and pressures are measured and inputted into the characterizing equations in order to generate the drift output voltages for modifying the output voltages of the plurality of sensors to compensate for the variations in operating temperatures and pressure.

Alternatively, a look-up table may be created prior to operation of the pneumatic manifold by inserting a range of ambient temperatures and pressures into the Flow Restrictor Equation. During operation, ambient temperature and pressure are measured and employed for accessing the corresponding drift voltage from the look-up table. Modified sensor output voltages are obtained by combining the sensor output voltages with the plurality of drift voltages. These steps are repeated continuously throughout operation of the pneumatic manifold to ensure real-time compensation for ambient temperature and pressure changes.

In order to control fluid flow through the flow restrictor, the modified pressure sensor output voltage is employed as a feedback control signal for opening and closing a proportional valve between the source of fluid and the flow restrictor.

The flow restrictor, pressure and temperature sensors may be thermally coupled to minimize errors caused by temperature variations and to simplify the firmware model.

Other aspects and advantages of the present invention will become apparent from the following detailed description, taken in conjunction with the accompanying drawings, illustrating by way of example the principles of the invention.

DETAILED DESCRIPTION OF THE PREFERRED EMBODIMENTS

Figure 2:
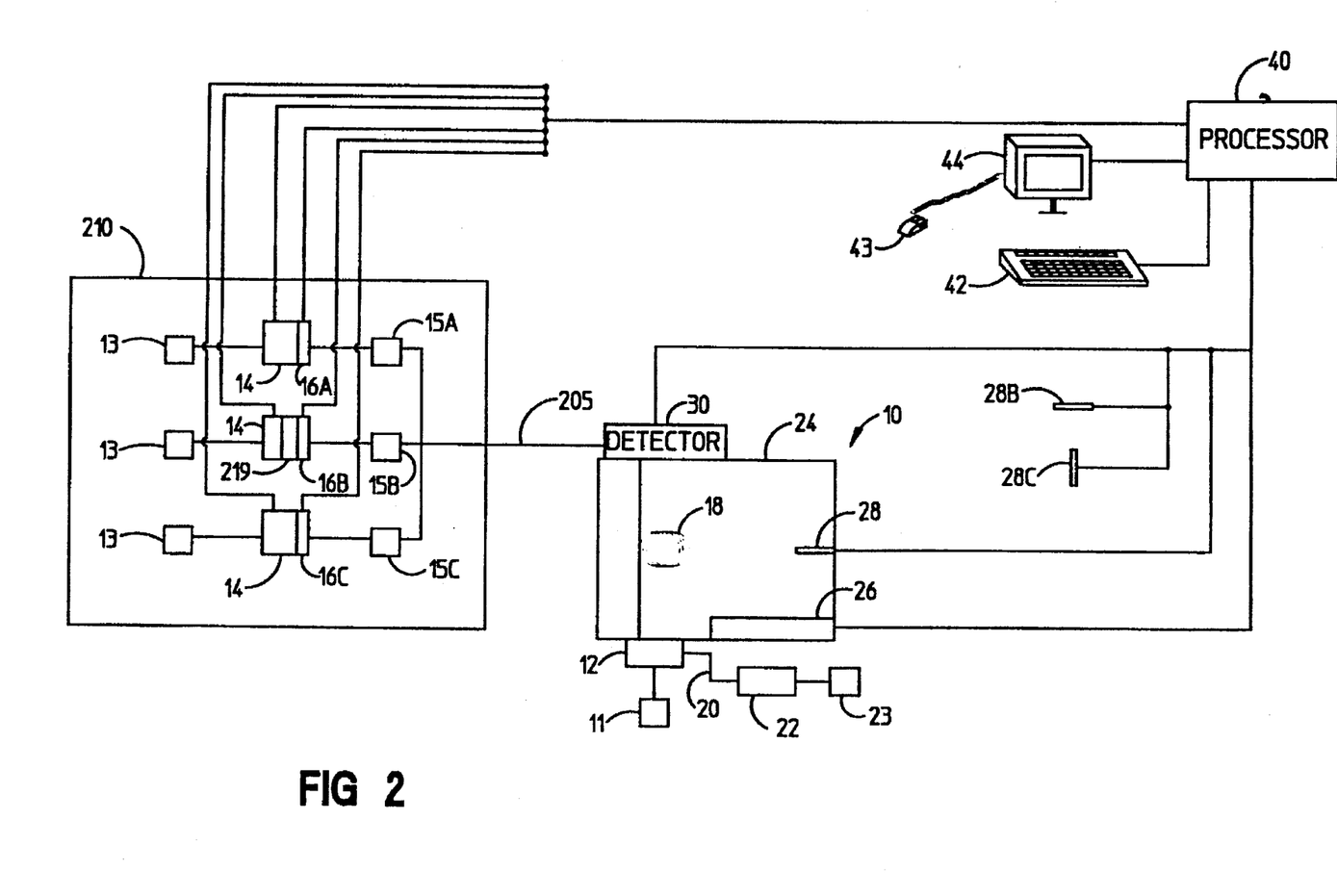
FIG. 2 is a simplified schematic representation a gas chromatograph having three detectors with electronically controlled support fluids in accordance with the preferred embodiment of the invention.

FIG. 2 illustrates a preferred embodiment of the invention as embodied in a gas chromatograph 10 having electronic pressure control with ambient temperature and pressure compensation of the pressure and flow of detector support fluids 205. A detector pneumatic manifold 210 typically supplies three fluid sources 13a, 13b, 13a to three separate valves 14a, 14b, 14c. The valves serve to control the pressure and the resulting flow rate of the support fluid through the flow restrictors 15a, 15b, 15c. The pressure sensors 16a, 16b, 16c provide stable output voltage levels in relation to the pressure of their corresponding support fluids. A temperature sensor 219 is coupled to pressure sensor 16b. All of the pressure sensors 16a, 16b, 16c and the flow restrictor are mounted on a thermally conductive bar such that the output voltage of the temperature sensor 219 represents the temperature of all of the pressure sensors and the flow sensor.

Figure 3:
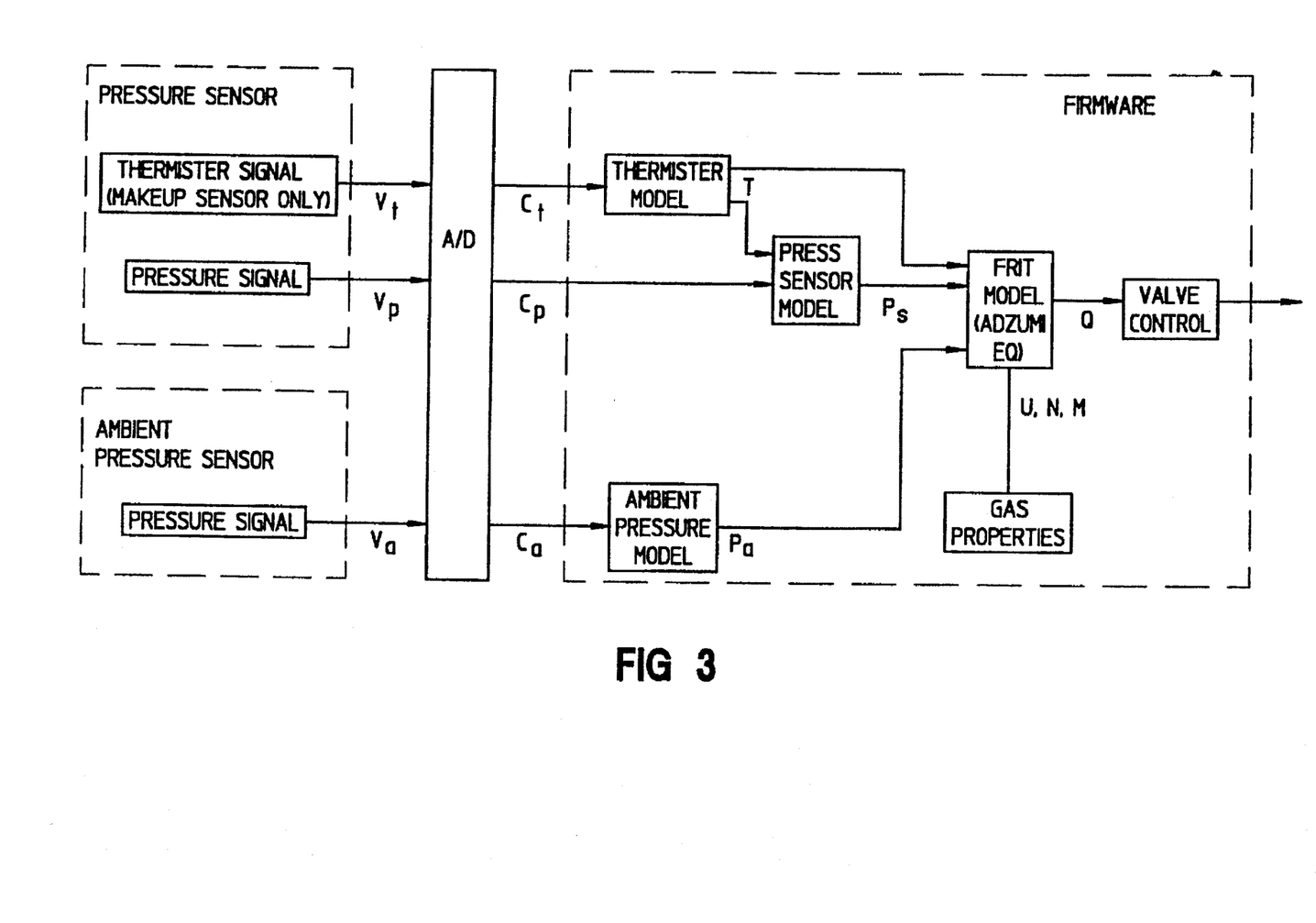
FIG. 3 is a block diagram depicting the relationship between the firmware models.

In order to provide compensation, a plurality of drift voltages are calculated by inputting current temperature and pressure values into four firmware models which characterize the effects of ambient pressure and temperature changes on fluid flow restrictor, effects of temperature on pressure sensor and temperature sensor output. Once calculated, the drift voltages are added to the sensors 16a–c output voltages to ensure proper control of the corresponding proportional valve. The relationship between these numerical models is illustrated in FIG. 3. A detector typically has one or more support fluids, each of which will require one or more numerical models to provide adequate compensation.

II. Derivation of Flow Restrictor, Temperature Sensor and Pressure Sensor Model

1. Flow Restrictor Model

The Flow restrictor model is based on the work of A. E. Scheidegger entitled "The Physics of Flow Through a Porous Media", University of Toronto Press, Toronto 1974, PP172, in which:

$$v = \frac{\pi \cdot E \cdot dpr}{8 \cdot A \cdot ug} + e \cdot \left(\frac{4}{3}\right) \cdot \sqrt{2 \cdot \pi} \cdot \sqrt{R \cdot \frac{Tg}{M}} \cdot \frac{F}{A \cdot pr} \cdot dpr$$

Where:

v="Seepage velocity"

e=Adzumi constant=0.9

A=Cross-sectional area of the porous media $$E = \frac{N \cdot r^4}{t} \quad N = \text{number of pores in area } A$$

$r$ = average radius of pores $$F = \frac{N \cdot r^3}{t} \quad t = \text{thickness of porous media}$$

R=universal gas constant

M=Molecular weight of the gas ug=Gas viscosity pr=Gas pressure dpr=Delta pr

Tg=Gas temperature

This equation can be modified to model fluid flow through a flow restrictor to provide:

$$Q = \frac{[\alpha]}{U \cdot T_f^{N+1}} \cdot (P_s^2 - P_a^2) + \frac{[\beta]}{(M \cdot T_f)^{.5}} \cdot (P_s - P_a)$$

Where:

Q=gas flow (sccm)

$P_s$=source pressure (psia)=[gage pressure]+[atmos pressure]

$P_a$=downstream pressure (psia)=[normally atoms pressure]

$T_f$=temperature of frit (degK)=degC]+273.18

U,N=viscosity constants which depend on the gas (viscosity in micropoises)

M=molecular weight of gas alpha=constant which is a property of the restrictor and is determined through calibration beta=constant which is a property of the restrictor and is determined through calibration The equation can be modified for use by firmware to provide:

$$Q = [\alpha f] * \frac{(P_s + P_a)^2 - P_a^2}{T_f^n} + [\beta f] * \frac{P_s}{T_f^5}$$

where:

$P_s$=source gauge pressure (psig)=$P_s$−[atmos pressure]

$\alpha f = [\alpha]/U$ $\beta f = [\beta]/(M^{0.5})$ n=N+1

The constants "$\alpha f$" and "$\beta f$", are determined by running each manifold through a calibration procedure at two known flow rates such that the output voltages corresponding to the flow rates can be substituted into the flow equation for determining the constants. Once the constants have been determined for each flow restrictor (and for each type of fluid flowing through the flow restrictor), they are substituted back into the models and the complete models are stored for retrieval during system operation. In the preferred embodiment, atmospheric pressure is used to approximate the pressure downstream from the flow restrictor. Thus, an error term will be introduced to the extent that there is a pressure drop downstream of the flow restrictor. In an alternative embodiment, a downstream pressure sensor may be included to provide actual downstream pressure into the flow restrictor model for more accurate compensation of downstream pressure drops.

2. Temperature Sensor Model

The temperature of the flow restrictor effects fluid flow through the flow restrictor. A temperature sensor model is developed which characterizes the response relationship between flow restrictor temperature and the output of a temperature sensor mounted in thermal contact with the flow restrictor. A linear approximation of this response relationship necessitates only two calibration points, in particular:

$$C_t = E + F * t_c$$

where:

$C_t$=thermistor response (A/D counts) E=offset at 0 degC (A/D counts), F=temperature sensitivity (A/D counts per degC) and $t_c$=calibration temperature.

3. Upstream Pressure Sensor Model

A model of the response relationship between the upstream pressure sensor and the pressure source and the temperature of the pressure sensor may be characterized as:

$$C_p = A + C * t_c + (B + D * t_c) * p_1$$

where:

$C_p$=sensor response (A/D counts)

A=offset at 0 degC and 0 psig (A/D counts)

B=pressure sensitivity (counts/psi)

$p_1$=source gauge pressure (psig)=$P_s$−[atmos pressure]

to=thermistor temperature (deg C)

The first derivative of the pressure sensor equation ($dC_p/dt_c$) is a function of pressure and characterizes the drift of the pressure sensor output signal (or temperature sensitivity), in particular:

$$dC_p/dt_c = C + D * p_1$$

Where:

C=temperature sensitivity (A/D counts per degC)

D=pressure sensitivity change with temperature (A/D counts per psi per deg C.)

Combining equations are rearranging: The constants A,B, C, &D are determined by calibration in the manner set forth below.

III. Calibration Procedure

Figure 4:
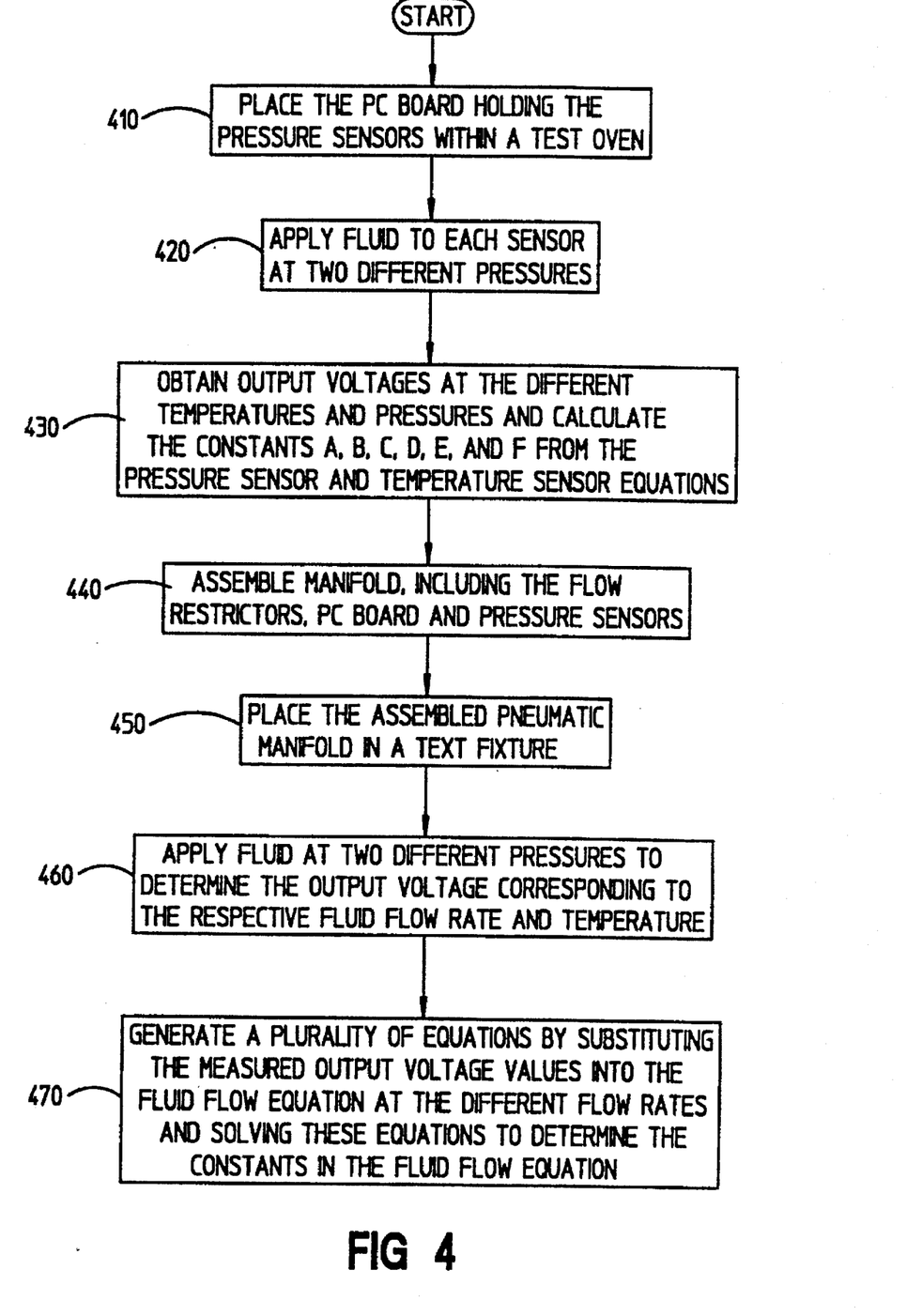
FIG. 4 is a flow chart illustrating the calibration procedure.
Figure 5A:
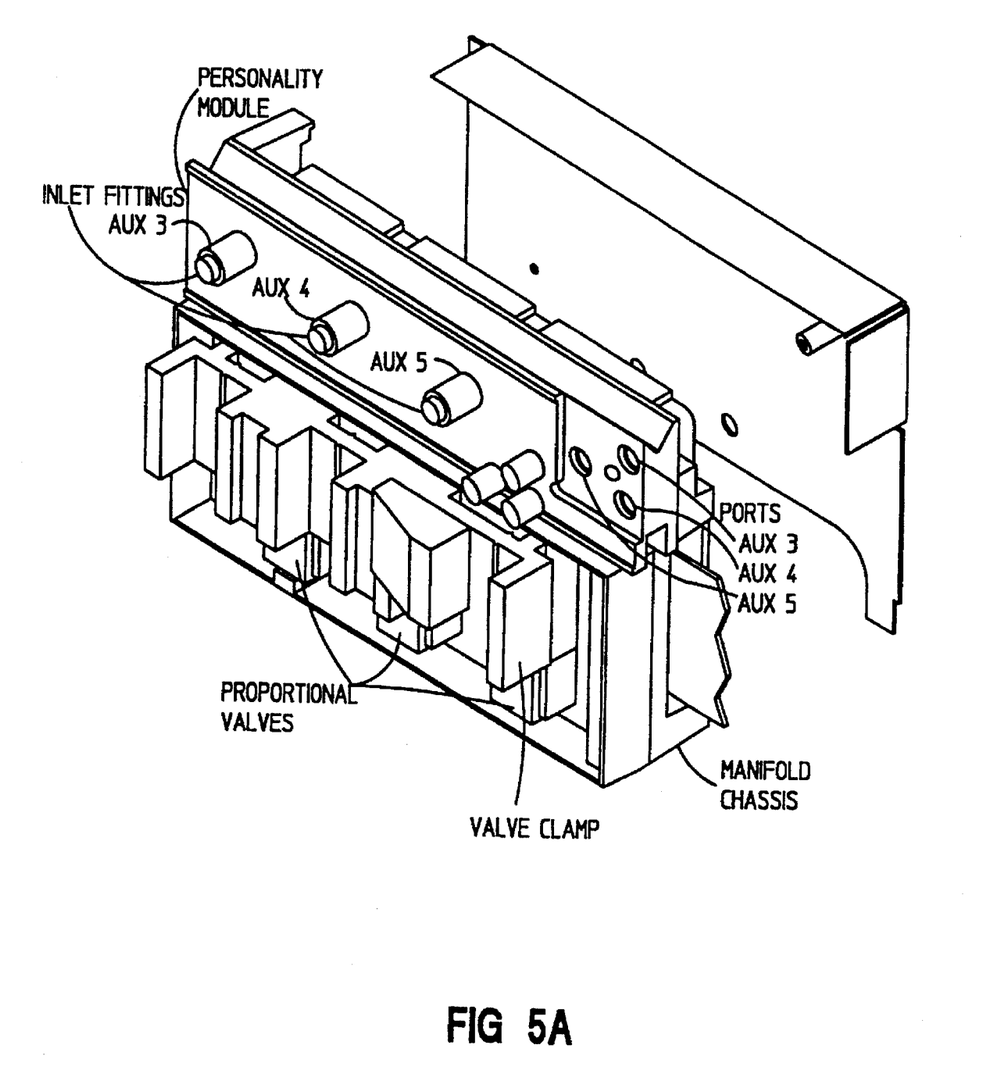
FIG. 5A is a perspective view of a front side view of a detector manifold.
Figure 5B:
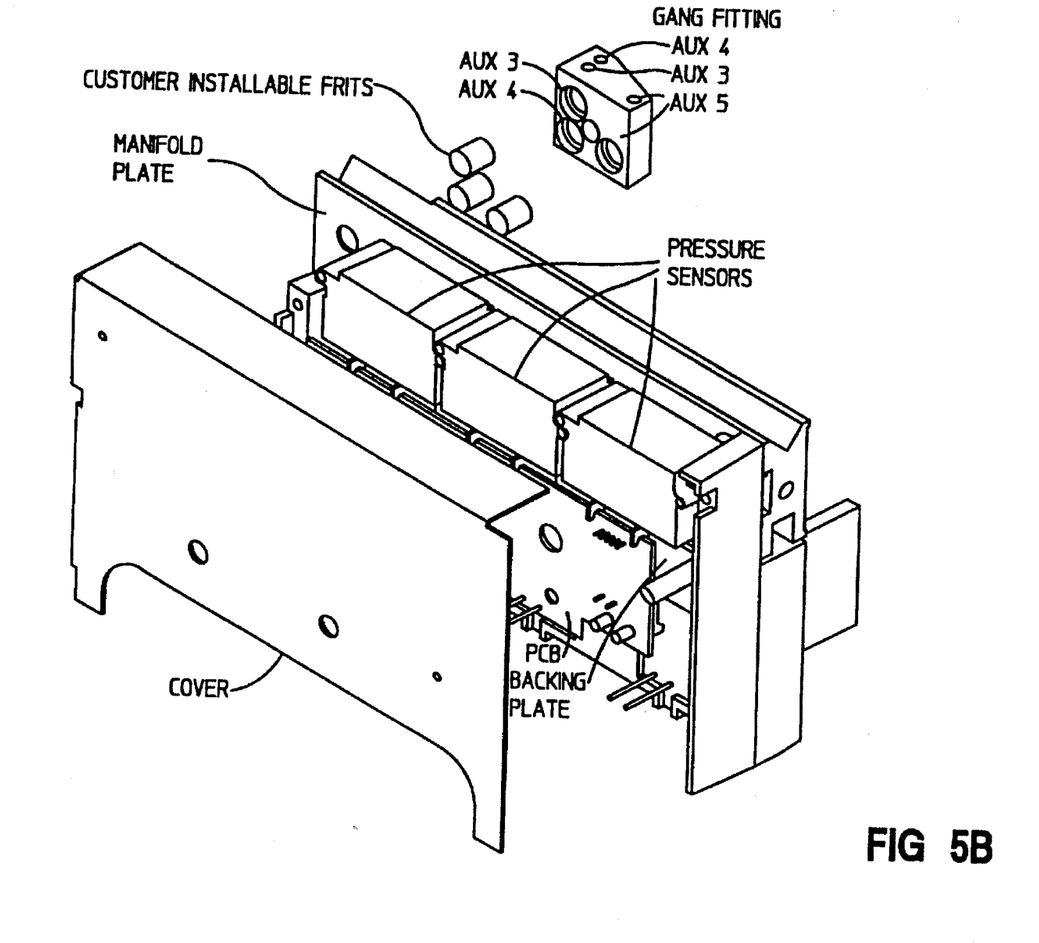
FIG. 5B is a perspective view of a back side view of a detector manifold.

FIG. 4 is a flow chart illustrating the steps in the calibration procedure. At step 410, a PC board holding the pressure sensors is placed within a test oven; at step 420, fluid is applied to each sensor at two different pressures; at step 430 the output voltages obtained at the different temperatures and pressures are employed for calculating the constants A, B, C, D, E and F from the Pressure sensor and Temperature sensor equations; at step 440, the manifold FIG. 5A and 5 is assembled and includes the flow restrictors, PC board and pressure sensors; at step 450, the assembled pneumatic manifold is placed in a text fixture; at step 460, fluid is applied at two different pressures and the output voltage corresponding to the respective fluid flow rate and temperature; and at step 470, a plurality of equations are generated by substituting in the measured output voltage values into the fluid flow equation at the different flow rates, these equations are solved simultaneously to determine the constants in the fluid flow equation.

The firmware models include unknown constants which must be determined for each type of detector support fluid.

In particular, for each pressure sensor, the pressure sensor output voltage Vo is measured (relating pressure to A/D counts) at two pressures (one of which can be 0 psig), each of which are conducted at two different temperatures representing the anticipated GC temperature operating range (one temperature nominally 35 deg). For each flow restrictor, pressure sensor output voltages Vo data is obtained to characterize fluid flow versus pressure at two flow rates other than zero flow and at a nominal 35 deg C. Such data is required for each fluid used in the channel. For the Thermistor Model, data must be gathered which characterizes temperature sensor temperature vs A/D converter counts at two different temperatures.

In an alternative embodiment of the invention, the flow restrictor and the pressure sensor each include a temperature sensor such that they do not have to be thermally coupled. The firmware model must be modified accordingly. Additionally, a pressure sensor could be added to the downstream side of the flow restrictor to replace the ambient pressure measurement.

IV. ELECTRONICS

Figure 6:
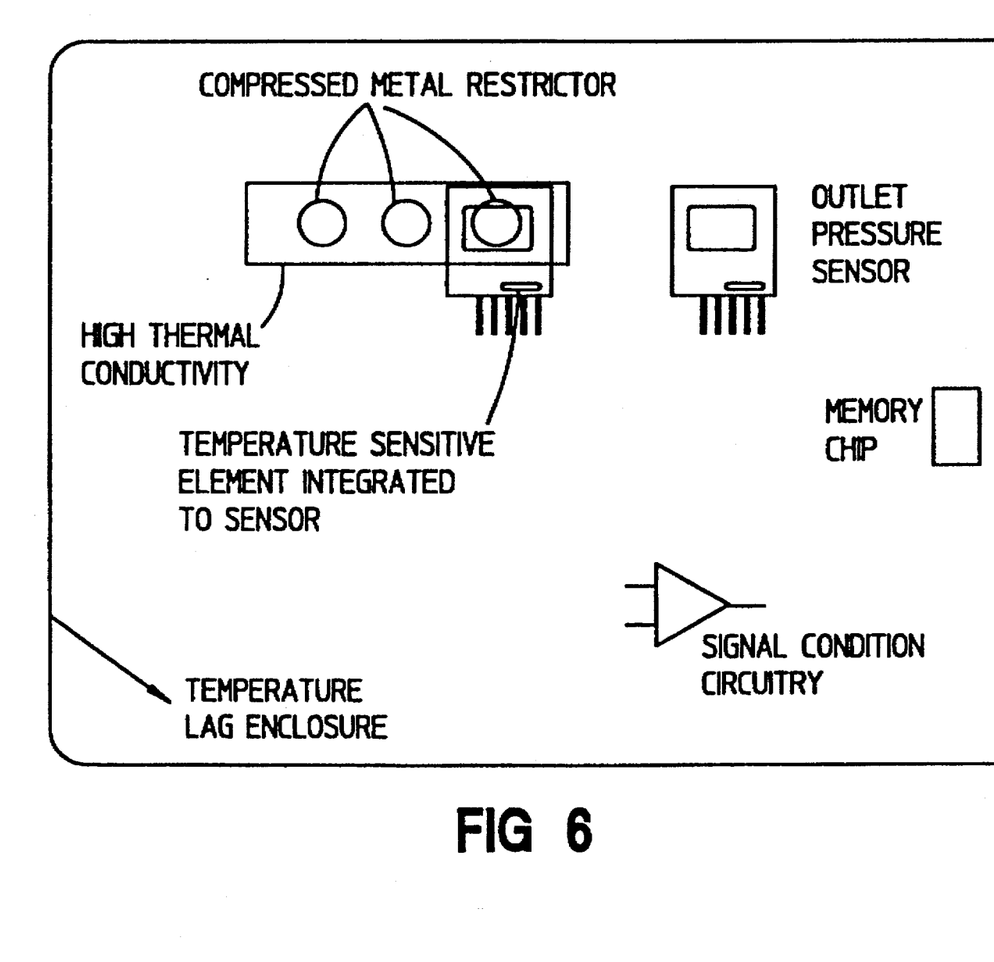
FIG. 6 is a typical configuration of the hardware.

FIG. 6 illustrates a typical configuration of the hardware portion of the invention. Several flow restrictors are shown coupled thermally to each other through a high thermal conductive bar. Aluminum is the construction material. Only one pressure sensor is shown mounted on the unit, which measures the upstream pressure of a flow restrictor. The pressure sensor is mounted to provide intimate thermal contact with the conductive bar. In the preferred embodiment, the low pressure side of all the flow restrictors are vented to ambient. A single ambient pressure sensor is employed and the measured pressure signal is used for all measurements. When the low pressure side of the restrictors are not at the same pressure multiple pressure sensors may be required.

In summary, the steps employed for generating a characteristic equation include:

Measure flow at two temperature and pressure points to calculate $\alpha$, $\beta$ and tempco; Linearize for small flow and pressure range; measure da/dT and db/dT for temperature compensation, and calculate da/dT and db/dT from characteristic flow equation.

Figure 7:
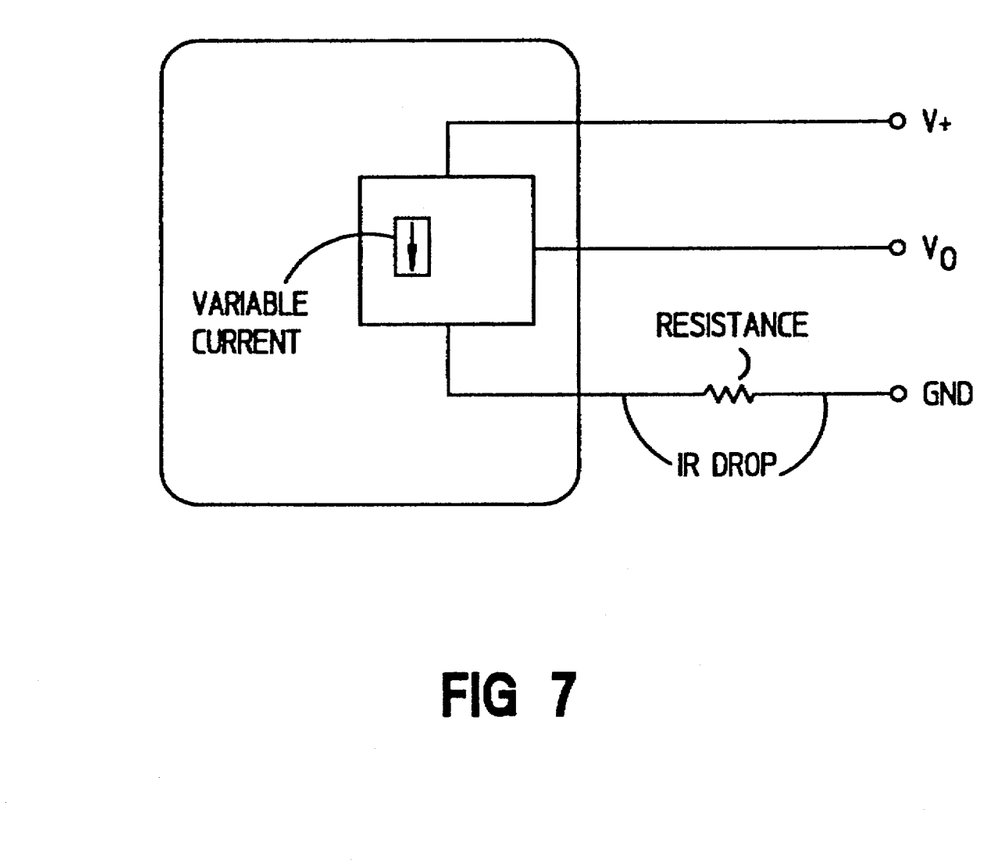
FIG. 7 is a schematic diagram of a prior art sensor with variable return current.

FIG. 7 shows the schematic drawing of a Prior Art sensor with variable return current. The voltage (IR) drop, due to this return current and any intrinsic resistance affects the sensor output voltage Vo in relation to ground. The use of surface mount technology increase circuit density such that conductor width on printed circuit boards decreases. For example, a typical trace width of 0.008" on a 0.5 oz copper printed circuit board contribute resistance of 60 milli ohm per inch. The connect resistance of a connector can also vary by tens of milliohms. Voltage drops stemming from intrinsic resistance can seriously affect signal integrity at micro volt and even milli-volt levels. While current loops are insensitive to conductor resistance and are used extensively for remote signal transmission, the bandwidth is limited. Although active ground circuitry is often used, such circuitry may pose stability problems. A high bandwidth design is also required to achieve a good active ground. Additionally, active circuitry does not eliminate the voltage drop across the sensor connector.

Figure 8:
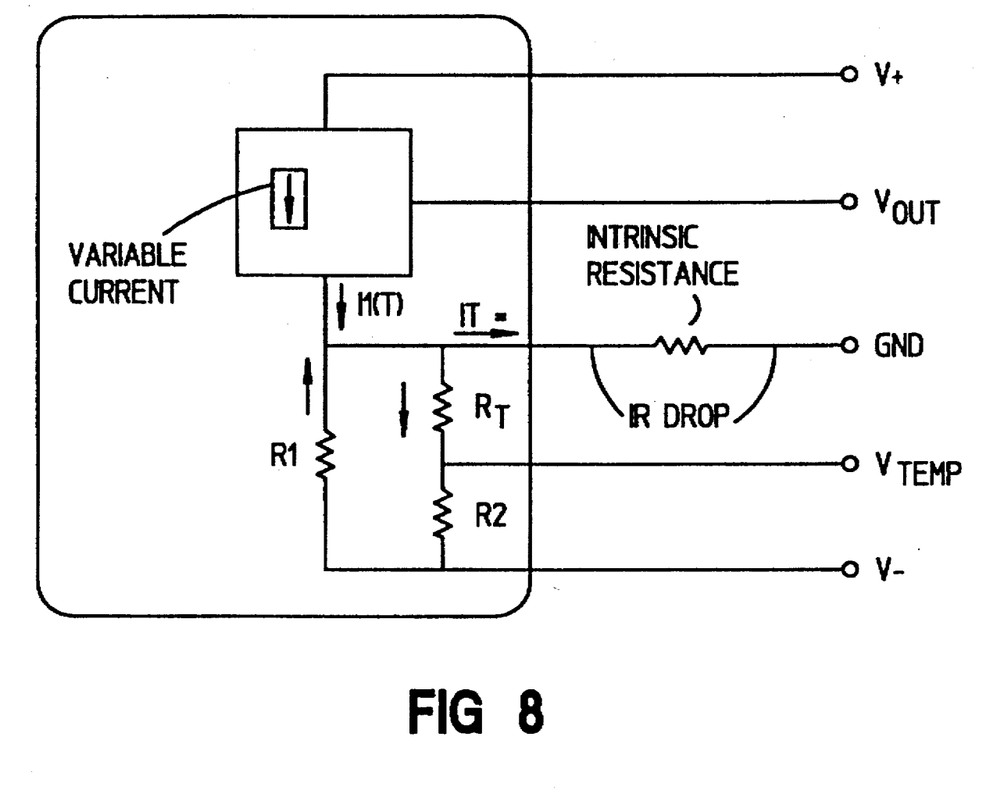
FIG. 8 is a schematic diagram of a sensor with return current balancing circuitry.

FIG. 6 illustrates the preferred embodiment in which a temperature sensor is integrated with a pressure sensor to provide good thermal matching between pressure and temperature sensing. The temperature sensor can also be mounted by other means as long as it is in good thermal contact with the conductive bar. FIG. 8 illustrates a return current balancing circuit employing a temperature sensitive resistor (Rt) and fixed resistors R1 and R2 that provides both a temperature output and good current mathcing over a wide temperature range.

The key advantage is the simplicity of the design. By not heating the components, an increased operating temperature range is achieved. A lower operating temperature than thermal zone improves reliability. There is no start-up time for the module since temperature of the module is kept at equilibrium at all time. There is also improved temperature performance since there is no temperature gradient due to the local heating of the heated component.

Calibration reduces accuracy requirement on voltage references and analog components. This can be explained by assuming that an A/D is used as part of the data acquisition system, Vo of the sensors can be measured as a portion of the reference voltage. If both the A/D and the voltage reference are derived from the same source, the accuracy, temperature drift and low frequency noise of the reference source is not important. All temperature drift due to individual components on the module are lumped together as a single temperature drift term and calibrated out.

The current balancing circuit shown in FIG. 8 reduces ground current over a wide temperature range by using temperature sensitive components to cancel ground current over a wide range of temperature. In our design, passive circuitry is used. It allows the sensor to run at its full bandwidth without interaction with an active ground circuit which can cause stability and transient problems. Passive circuits are less problematic with RF immunity and are more reliable.

While the invention has been described and illustrated with reference to specific embodiments in the area of gas chromatography, those skilled in the art will recognize that modification and variations may be made such that the invention is equally applicable to the field of automotive engine design, or other fields where compensation for changes in ambient temperatures and pressures is required for measurement and control of fluid supplies. For example, the fuel/air mixture of an automotive engine is typically controlled by measuring air flow through an intake manifold and then controlling the amount of fuel injected into the intake manifold. The invention is very applicable to this application an may be employed to enhance engine operating efficiency and performance.

What is claimed is:

1. An electronically controlled pneumatic manifold which regulates the flow rate of fluid flowing through a flow restrictor to a desired flow rate by calculating the actual flow rate and generating a control signal, compensated for the effects of ambient temperature and pressure changes, which adjusts the opening of a control valve to adjust the pressure, and the corresponding flow rate, of the fluid flowing through the flow restrictor to the desired flow rate, comprising:

a computer having a memory, a manifold body made of heat conductive material, a flow restrictor mounted in thermal contact with said manifold body, said flow restrictor having a high pressure side in contact with the fluid source and a low pressure slide, a fluid pressure sensor, mounted in thermal contact with said manifold body, for generating a fluid pressure signal corresponding to the pressure of the fluid between the control valve and the flow restrictor, an ambient pressure sensor, mounted in thermal contact with said manifold body, for generating an ambient pressure signal corresponding to the ambient pressure, a temperature sensor, mounted in thermal contact with said manifold body, for generating a temperature signal corresponding to the temperature of the manifold, a flow restrictor model which characterizes fluid flow through the flow restrictor in terms of the ambient pressure signal, the temperature signal, and the fluid pressure signal, the flow restrictor model being stored on the computer, such that the computer can calculate the actual flow rate based on the measured signals, wherein the computer generates a control signal for adjusting fluid flow from the calculated flow rate to the desired flow rate.

2. An electronically controlled pneumatic manifold as claimed in claim 1, further comprising an electronic control valve mounted in thermal contact with said manifold body, for adjusting the opening of the control valve in response to said control signal.

3. The electronically controlled pneumatic manifold as claimed in claim 1, an equation for modeling flow through a flow restrictor in which fluid flow varies in accordance with the formula:

$$Q = [\alpha f] * \frac{(P_s + P_a)^2 - P_a^2}{T_f} + [\beta f] * \frac{P_s}{T_f^5}$$

Where:

Q=gas flow (sccm)

$P_s$=source pressure (psia)=[gauge pressure]+[atmos pressure]

$P_a$=downstream pressure (psia)=[normally atoms pressure]

$T_f$=temperature of frit (degK)=degC+273.18

U,N=viscosity constants which depend on the gas (viscosity in micropoises)

M=molecular weight of gas $p_i$=source gauge pressure (psig)=$P_s$−[atmos pressure]

$\alpha f = [\alpha]/U$ $\beta f = [\beta]/(M^{0.5})$ $n = N+1$.

4. The electronically controlled pneumatic manifold as claimed in claim 1, the fluid pressure signal response in A/D counts of the flow restrictor model varying in accordance with the formula, $$C_p = A + C*t_c + (B + D*t_c)*p_1,$$

where:

A=offset at 0 degC and 0 psig (A/D counts)

B=pressure sensitivity (counts/psi)

C=temperature sensitivity (A/D counts per degC)

D=pressure sensitivity change with temperature (A/D counts per psi per degC)

$p_1$=Source gauge pressure (psig)=$P_s$-[atmos pressure]

$t_c$=thermistor temperature (deg C).

5. The electronically controlled pneumatic manifold as claimed in claim 1, further comprising a temperature sensor model characterizes the response relationship between the flow restrictor temperature and the output of the temperature sensor mounted in thermal contact with the flow restrictor, wherein the temperature of the flow restrictor $C_t$ in A/D counts is equal to E+F*$T_c$ and, E=offset at 0 degC (A/D counts), F=temperature sensitivity (A/D counts per degC) and $T_c$=calibration temperature.

6. The electronically controlled pneumatic manifold as claimed in claim 1, further comprising an ambient pressure sensor which generates an ambient pressure signal proportional to atmospheric pressure in accordance with the relationship Pa=j(Ca).

7. The electronically controlled pneumatic manifold as claimed in claim 6, wherein, the ambient pressure sensor A/D voltage to counts relationship Ca is equal to k(Va), the source pressure A/D voltage to counts relationship Cp is equal to m(Vp), the temperature sensor voltage to A/D counts Ct is equal to n(Vt).

8. The electronically controlled pneumatic manifold as claimed in claim 1, further comprising a plurality of flow restricting flow restrictors mounted on a thermally conductive surface.

9. The electronically controlled pneumatic manifold as claimed in claim 8, wherein said thermally conductive surface is made of aluminum.

10. An electronically controlled pneumatic manifold as recited in claim 1, further comprising:

an A/D converter switchably connected to said fluid pressure signal and said ambient pressure signal;

a reference voltage connected to the fluid pressure sensor and the ambient pressure sensor for sourcing current to the sensor;

a first return current, proportional to ambient temperature, flowing out of the fluid pressure sensor;

a first return path having intrinsic resistance, connected between said fluid pressure sensor and said A/D converter, whereby any current flowing through said first return path introduces error into said fluid pressure signal;

a first variably resistive circuit connected to the fluid pressure sensor, wherein the current flowing though said circuit varies proportionally with ambient temperature, so that the current flowing through said first return path is substantially zero over a range of ambient temperatures and substantially no temperature error is introduced into said fluid pressure signal;

a second return current, proportional to ambient temperature, flowing out of the ambient pressure sensor;

a second return path having intrinsic resistance, connected between said ambient pressure sensor and said A/D converter, whereby any current flowing through said first return path introduces error into said ambient pressure signal; and a second variably resistive circuit connected to the ambient pressure sensor, wherein the current flowing though said circuit varies proportionally with ambient temperature, so that the current flowing through said second return path is substantially zero over a range of ambient temperatures and substantially no temperature error is introduced into said ambient pressure signal.

* * * * *